United States Patent
Lazdunski et al.

(10) Patent No.: US 6,962,976 B2
(45) Date of Patent: Nov. 8, 2005

(54) HUMAN TREK2, A STRETCH- AND ARACHIDONIC ACID-SENSITIVE K+ CHANNEL ACTIVATED BY INHALATIONAL ANESTHETICS AND NILUZOLE

(75) Inventors: Michel Lazdunski, Nice (FR); Florian Lesage, Nice (FR); Georges Romey, Nice (FR)

(73) Assignee: Centre National de la Recherche Scientifique-CNRS (FR)

( * ) Notice: Subject to any disclaimer, the term of this patent is extended or adjusted under 35 U.S.C. 154(b) by 432 days.

(21) Appl. No.: 09/892,360

(22) Filed: Jun. 27, 2001

(65) Prior Publication Data

US 2004/0101833 A1 May 27, 2004

Related U.S. Application Data

(60) Provisional application No. 60/214,559, filed on Jun. 27, 2000.

(51) Int. Cl.[7] .......................... C07K 2/00; C07K 14/00; A61K 38/17
(52) U.S. Cl. ........................ 530/350; 530/300; 514/12; 424/198.1
(58) Field of Search ................................. 530/300, 350; 514/2, 12; 424/85.1, 198.1; 435/4

(56) References Cited

U.S. PATENT DOCUMENTS 6,242,217 B1 * 6/2001 Meadows et al. .......... 435/69.1

OTHER PUBLICATIONS

Fink et al. A neuronal two P domain K+ channel stimulated by arachidonic acid and polyunsaturated fatty acids.☐☐ EMBO J. 17(12):3297–3308, 1998.*

Fink et al. Cloning, functional expression and brain localization of a novel unconventional outward rectifier K+ channel. EMBO J. 15(24): 6854–6862, 1996.*

Gu et al. Expression pattern and functional characteristics of two novel splice variants of the two–pore–domain potassium channel TREK–2. J Physiol. 539(Pt. 3):657–668, 2002.*

Lesage et al. Molecular and functional properties of two–pore–domain potassium channels. Am J Physiol Renal Physiol. 279(5):F793–801, 2000.*

Lesage et al. Human TREK2, a 2P domain mechano–sensitive K+ channel with multiple regulations by polyunsaturated fatty acids, lysophospholipids, and Gs, Gi, and Gq protein–coupled receptors. J Biol Chem. 275(37):28398–28405, 2000.*

Lesage et al. TWIK–1, a ubiquitous human weakly inward rectifying K+ channel with a novel structure. EMBO J. 15(5):1004–1011, 1996.*

Maylie et al. Beam me up, Scottie! TREK channels swing both ways. Nat Neurosci. 4(5):457–458, 2001.*

Patel et al. A mammalian two pore domain mechano–gates S–like K+ channel. EMBO J. 17(15):4283–4290, 1998.*

Patel et al. Inhalational anesthetics activate two–pore–domain background K+ channels. Nat Neurosci. 2(5):422–426, 1999.*

* cited by examiner

*Primary Examiner*—Elizabeth Kemmerer
*Assistant Examiner*—Bridget E. Bunner
(74) *Attorney, Agent, or Firm*—DLA Piper Rudnick Gray Cary US LLP

(57) ABSTRACT

This invention relates to a protein including a mammalian K+ channel with two pore domains, designated TREK2, that produces currents whose current-voltage relationship is weakly inward rectifying in high symmetrical K+ conditions. This invention further relates to the isolation and characterization of such protein, as well as a method using TREK2 to identify bioactive compounds having anesthetic properties.

4 Claims, 7 Drawing Sheets

SEQUENCE LISTING

<160> NUMBER OF SEQ ID NOS: 25

<210> SEQ ID NO 1
<211> LENGTH: 1614
<212> TYPE: DNA
<213> ORGANISM: Homo sapiens
<220> FEATURE:
<221> NAME/KEY: CDS
<222> LOCATION: (1)..(1614)
<223> OTHER INFORMATION: ORF of human TREK2 cDNA

<400> SEQUENCE: 1

```
atg ttt ttt ctc tac aca gac ttc ttt ctt tcc ttg gtg gcc gtt ccc      48
Met Phe Phe Leu Tyr Thr Asp Phe Phe Leu Ser Leu Val Ala Val Pro
  1               5                  10                  15 gca gca gca ccg gtg tgc cag ccc aag agc gcc act aac ggg caa ccc      96
Ala Ala Ala Pro Val Cys Gln Pro Lys Ser Ala Thr Asn Gly Gln Pro
```

-continued

|  |  | 20 |  |  |  | 25 |  |  |  | 30 |  |  |  |  |
|---|---|---|---|---|---|---|---|---|---|---|---|---|---|---|

```
ccg gct ccg gct ccg act cca act ccg cgc ctg tcc att tcc tcc cga       144
Pro Ala Pro Ala Pro Thr Pro Thr Pro Arg Leu Ser Ile Ser Ser Arg
        35                  40                  45 gcc aca gtg gta gcc agg atg gaa ggc acc tcc caa ggg ggc ttg cag       192
Ala Thr Val Val Ala Arg Met Glu Gly Thr Ser Gln Gly Gly Leu Gln
    50                  55                  60 acc gtc atg aag tgg aag acg gtg gtt gcc atc ttt gtg gtt gtg gtg       240
Thr Val Met Lys Trp Lys Thr Val Val Ala Ile Phe Val Val Val Val
65                  70                  75                  80 gtc tac ctt gtc act ggc ggt ctt gtc ttc cgg gca ttg gag cag ccc       288
Val Tyr Leu Val Thr Gly Gly Leu Val Phe Arg Ala Leu Glu Gln Pro
            85                  90                  95 ttt gag agc agc cag aag aat acc atc gcc ttg gag aag gcg gaa ttc       336
Phe Glu Ser Ser Gln Lys Asn Thr Ile Ala Leu Glu Lys Ala Glu Phe
                100                 105                 110 ctg cgg gat cat gtc tgt gtg agc ccc cag gag ctg gag acg ttg atc       384
Leu Arg Asp His Val Cys Val Ser Pro Gln Glu Leu Glu Thr Leu Ile
            115                 120                 125 cag cat gct ctt gat gct gac aat gcg gga gtc agt cca ata gga aac       432
Gln His Ala Leu Asp Ala Asp Asn Ala Gly Val Ser Pro Ile Gly Asn
    130                 135                 140 tct tcc aac aac agc agc cac tgg gac ctc ggc agt gcc ttt ttc ttt       480
Ser Ser Asn Asn Ser Ser His Trp Asp Leu Gly Ser Ala Phe Phe Phe
145                 150                 155                 160 gct gga act gtc att acg acc ata ggg tat ggg aat att gct ccg agc       528
Ala Gly Thr Val Ile Thr Thr Ile Gly Tyr Gly Asn Ile Ala Pro Ser
                165                 170                 175 act gaa gga ggc aaa atc ttt tgt att tta tat gcc atc ttt gga att       576
Thr Glu Gly Gly Lys Ile Phe Cys Ile Leu Tyr Ala Ile Phe Gly Ile
                180                 185                 190 cca ctc ttt ggt ttc tta ttg gct gga att gga gac caa ctt gga acc       624
Pro Leu Phe Gly Phe Leu Leu Ala Gly Ile Gly Asp Gln Leu Gly Thr
        195                 200                 205 atc ttt ggg aaa agc att gca aga gtg gag aag gtc ttt cga aaa aag       672
Ile Phe Gly Lys Ser Ile Ala Arg Val Glu Lys Val Phe Arg Lys Lys
    210                 215                 220 caa gtg agt cag acc aag atc cgg gtc atc tca acc atc ctg ttc atc       720
Gln Val Ser Gln Thr Lys Ile Arg Val Ile Ser Thr Ile Leu Phe Ile
225                 230                 235                 240 ttg gcc ggc tgc att gtg ttt gtg acg atc cct gct gtc atc ttt aag       768
Leu Ala Gly Cys Ile Val Phe Val Thr Ile Pro Ala Val Ile Phe Lys
                245                 250                 255 tac atc gag ggc tgg acg gcc ttg gag tcc att tac ttt gtg gtg gtc       816
Tyr Ile Glu Gly Trp Thr Ala Leu Glu Ser Ile Tyr Phe Val Val Val
                260                 265                 270 act ctg acc acg gtg ggc ttt ggt gat ttt gtg gca ggg gga aac gct       864
Thr Leu Thr Thr Val Gly Phe Gly Asp Phe Val Ala Gly Gly Asn Ala
        275                 280                 285 ggc atc aat tat cgg gag tgg tat aag ccc cta gtg tgg ttt tgg atc       912
Gly Ile Asn Tyr Arg Glu Trp Tyr Lys Pro Leu Val Trp Phe Trp Ile
    290                 295                 300 ctt gtt ggc ctt gcc tac ttt gca gct gtc ctc agt atg atc gga gat       960
Leu Val Gly Leu Ala Tyr Phe Ala Ala Val Leu Ser Met Ile Gly Asp
305                 310                 315                 320 tgg cta cgg gtt ctg tcc aaa aag aca aaa gaa gag gtg ggt gaa atc      1008
Trp Leu Arg Val Leu Ser Lys Lys Thr Lys Glu Glu Val Gly Glu Ile
                325                 330                 335 aag gcc cat gcg gca gag tgg aag gcc aat gtc acg gct gag ttc cgg      1056
```

```
                                                    -continued

Lys Ala His Ala Ala Glu Trp Lys Ala Asn Val Thr Ala Glu Phe Arg
            340                 345                 350 gag aca cgg cga agg ctc agc gtg gag atc cac gat aag ctg cag cgg      1104
Glu Thr Arg Arg Arg Leu Ser Val Glu Ile His Asp Lys Leu Gln Arg
        355                 360                 365 gcg gcc acc atc cgc agc atg gag cgc cgg cgg ctg ggc ctg gac cag      1152
Ala Ala Thr Ile Arg Ser Met Glu Arg Arg Arg Leu Gly Leu Asp Gln
    370                 375                 380 cgg gcc cac tca ctg gac atg ctg tcc ccc gag aag cgc tct gtc ttt      1200
Arg Ala His Ser Leu Asp Met Leu Ser Pro Glu Lys Arg Ser Val Phe
385                 390                 395                 400 gct gcc ctg gac acc ggc cgc ttc aag gcc tca tcc cag gag agc atc      1248
Ala Ala Leu Asp Thr Gly Arg Phe Lys Ala Ser Ser Gln Glu Ser Ile
                405                 410                 415 aac aac cgg ccc aac aac ctg cgc ctg aag ggg ccg gag cag ctg aac      1296
Asn Asn Arg Pro Asn Asn Leu Arg Leu Lys Gly Pro Glu Gln Leu Asn
            420                 425                 430 aag cat ggg cag ggt gcg tcc gag gac aac atc atc aac aag ttc ggg      1344
Lys His Gly Gln Gly Ala Ser Glu Asp Asn Ile Ile Asn Lys Phe Gly
        435                 440                 445 tcc acc tcc aga ctc acc aag agg aaa aac aag gac ctc aaa aag acc      1392
Ser Thr Ser Arg Leu Thr Lys Arg Lys Asn Lys Asp Leu Lys Lys Thr
    450                 455                 460 ttg ccc gag gac gtt cag aaa atc tac aag acc ttc cgg aat tac tcc      1440
Leu Pro Glu Asp Val Gln Lys Ile Tyr Lys Thr Phe Arg Asn Tyr Ser
465                 470                 475                 480 ctg gac gag gag aag aaa gag gag gag acg gaa aag atg tgt aac tca      1488
Leu Asp Glu Glu Lys Lys Glu Glu Glu Thr Glu Lys Met Cys Asn Ser
                485                 490                 495 gac aac tcc agc aca gcc atg ctg acg gac tgt atc cag cag cac gct      1536
Asp Asn Ser Ser Thr Ala Met Leu Thr Asp Cys Ile Gln Gln His Ala
            500                 505                 510 gag ttg gag aac gga atg ata ccc acg gac acc aaa gac cgg gag ccg      1584
Glu Leu Glu Asn Gly Met Ile Pro Thr Asp Thr Lys Asp Arg Glu Pro
        515                 520                 525 gag aac aac tca tta ctt gaa gac aga aac                              1614
Glu Asn Asn Ser Leu Leu Glu Asp Arg Asn
    530                 535

<210> SEQ ID NO 2
<211> LENGTH: 538
<212> TYPE: PRT
<213> ORGANISM: Homo sapiens

<400> SEQUENCE: 2

Met Phe Phe Leu Tyr Thr Asp Phe Phe Leu Ser Leu Val Ala Val Pro
  1               5                  10                  15

Ala Ala Ala Pro Val Cys Gln Pro Lys Ser Ala Thr Asn Gly Gln Pro
                 20                  25                  30

Pro Ala Pro Ala Pro Thr Pro Thr Pro Arg Leu Ser Ile Ser Ser Arg
             35                  40                  45

Ala Thr Val Val Ala Arg Met Glu Gly Thr Ser Gln Gly Gly Leu Gln
         50                  55                  60

Thr Val Met Lys Trp Lys Thr Val Val Ala Ile Phe Val Val Val
 65                  70                  75                  80

Val Tyr Leu Val Thr Gly Gly Leu Val Phe Arg Ala Leu Glu Gln Pro
                 85                  90                  95

Phe Glu Ser Ser Gln Lys Asn Thr Ile Ala Leu Glu Lys Ala Glu Phe
                100                 105                 110
```

-continued

```
Leu Arg Asp His Val Cys Val Ser Pro Gln Glu Leu Glu Thr Leu Ile
        115                 120                 125
Gln His Ala Leu Asp Ala Asp Asn Ala Gly Val Ser Pro Ile Gly Asn
    130                 135                 140
Ser Ser Asn Asn Ser Ser His Trp Asp Leu Gly Ser Ala Phe Phe Phe
145                 150                 155                 160
Ala Gly Thr Val Ile Thr Thr Ile Gly Tyr Gly Asn Ile Ala Pro Ser
                165                 170                 175
Thr Glu Gly Gly Lys Ile Phe Cys Ile Leu Tyr Ala Ile Phe Gly Ile
            180                 185                 190
Pro Leu Phe Gly Phe Leu Leu Ala Gly Ile Gly Asp Gln Leu Gly Thr
        195                 200                 205
Ile Phe Gly Lys Ser Ile Ala Arg Val Glu Lys Val Phe Arg Lys Lys
    210                 215                 220
Gln Val Ser Gln Thr Lys Ile Arg Val Ile Ser Thr Ile Leu Phe Ile
225                 230                 235                 240
Leu Ala Gly Cys Ile Val Phe Val Thr Ile Pro Ala Val Ile Phe Lys
                245                 250                 255
Tyr Ile Glu Gly Trp Thr Ala Leu Glu Ser Ile Tyr Phe Val Val Val
            260                 265                 270
Thr Leu Thr Thr Val Gly Phe Gly Asp Phe Val Ala Gly Gly Asn Ala
        275                 280                 285
Gly Ile Asn Tyr Arg Glu Trp Tyr Lys Pro Leu Val Trp Phe Trp Ile
    290                 295                 300
Leu Val Gly Leu Ala Tyr Phe Ala Ala Val Leu Ser Met Ile Gly Asp
305                 310                 315                 320
Trp Leu Arg Val Leu Ser Lys Lys Thr Lys Glu Val Gly Glu Ile
                325                 330                 335
Lys Ala His Ala Ala Glu Trp Lys Ala Asn Val Thr Ala Glu Phe Arg
            340                 345                 350
Glu Thr Arg Arg Arg Leu Ser Val Glu Ile His Asp Lys Leu Gln Arg
        355                 360                 365
Ala Ala Thr Ile Arg Ser Met Glu Arg Arg Leu Gly Leu Asp Gln
    370                 375                 380
Arg Ala His Ser Leu Asp Met Leu Ser Pro Glu Lys Arg Ser Val Phe
385                 390                 395                 400
Ala Ala Leu Asp Thr Gly Arg Phe Lys Ala Ser Ser Gln Glu Ser Ile
                405                 410                 415
Asn Asn Arg Pro Asn Asn Leu Arg Leu Lys Gly Pro Glu Gln Leu Asn
            420                 425                 430
Lys His Gly Gln Gly Ala Ser Glu Asp Asn Ile Ile Asn Lys Phe Gly
        435                 440                 445
Ser Thr Ser Arg Leu Thr Lys Arg Lys Asn Lys Asp Leu Lys Lys Thr
    450                 455                 460
Leu Pro Glu Asp Val Gln Lys Ile Tyr Lys Thr Phe Arg Asn Tyr Ser
465                 470                 475                 480
Leu Asp Glu Glu Lys Lys Glu Glu Thr Glu Lys Met Cys Asn Ser
                485                 490                 495
Asp Asn Ser Ser Thr Ala Met Leu Thr Asp Cys Ile Gln Gln His Ala
            500                 505                 510
Glu Leu Glu Asn Gly Met Ile Pro Thr Asp Thr Lys Asp Arg Glu Pro
        515                 520                 525
```

```
Glu Asn Asn Ser Leu Leu Glu Asp Arg Asn
    530                 535
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
actgccgagg tcccagtggc tgctgtt                                    27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
tctggctgct ctcaaagggc tgct                                       24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
gacgatccct gctgtcatct t                                          21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
ttgcagctgt cctcagtaga tcg                                        23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
tagaatcgag gtcgacggta tc                                         22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
gatttaggtg acactataga atcga                                      25

<210> SEQ ID NO 9
<211> LENGTH: 19
<212> TYPE: DNA

```
<213> ORGANISM: Artificial Sequence
<220> FEATURE:
<223> OTHER INFORMATION: Description of Artificial Sequence: Primer

<400> SEQUENCE: 9
cagccctttg agagcagcc                                                      19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
aagatgacag cagggatcgt c                                                   21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
gaggcccggc cagggatcc tg                                                   22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
ctcagtgctc accaccatcg                                                     20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
gaggcccggc cagggatcc tg                                                   22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gatccacctg caacgtagtc                                                     20

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
actgccgagg tcccagtggc tgctgtt                                             27
```

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
tcaggctgcc agctggactg                                               20

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
tagctgatct ccaactccag ccaag                                         25

<210> SEQ ID NO 18
<211> LENGTH: 411
<212> TYPE: PRT
<213> ORGANISM: Mus musculus

<400> SEQUENCE: 18
```

| Met | Ala | Ala | Pro | Asp | Leu | Leu | Asp | Pro | Lys | Ser | Ala | Ala | Gln | Asn | Ser |
|---|---|---|---|---|---|---|---|---|---|---|---|---|---|---|---|
| 1 | | | | 5 | | | | | 10 | | | | | 15 | |

| Lys | Pro | Arg | Leu | Ser | Phe | Ser | Thr | Lys | Pro | Thr | Val | Leu | Ala | Ser | Arg |
|---|---|---|---|---|---|---|---|---|---|---|---|---|---|---|---|
| | | | 20 | | | | | 25 | | | | | 30 | | |

| Val | Glu | Ser | Asp | Thr | Thr | Ile | Asn | Val | Met | Lys | Trp | Lys | Thr | Val | Ser |
|---|---|---|---|---|---|---|---|---|---|---|---|---|---|---|---|
| | | | 35 | | | | | 40 | | | | | 45 | | |

| Thr | Ile | Phe | Leu | Val | Val | Val | Leu | Tyr | Leu | Ile | Ile | Gly | Ala | Thr | Val |
|---|---|---|---|---|---|---|---|---|---|---|---|---|---|---|---|
| | 50 | | | | | 55 | | | | | 60 | | | | |

| Phe | Lys | Ala | Leu | Glu | Gln | Pro | His | Glu | Ile | Ser | Gln | Arg | Thr | Thr | Ile |
|---|---|---|---|---|---|---|---|---|---|---|---|---|---|---|---|
| 65 | | | | | 70 | | | | | 75 | | | | | 80 |

| Val | Ile | Gln | Lys | Gln | Thr | Phe | Ile | Ser | Gln | His | Ser | Cys | Val | Asn | Ser |
|---|---|---|---|---|---|---|---|---|---|---|---|---|---|---|---|
| | | | | 85 | | | | | 90 | | | | | 95 | |

| Thr | Glu | Leu | Asp | Glu | Leu | Ile | Gln | Gln | Ile | Val | Ala | Ala | Ile | Asn | Ala |
|---|---|---|---|---|---|---|---|---|---|---|---|---|---|---|---|
| | | | 100 | | | | | 105 | | | | | 110 | | |

| Gly | Ile | Ile | Pro | Leu | Gly | Asn | Thr | Ser | Asn | Gln | Ile | Ser | His | Trp | Asp |
|---|---|---|---|---|---|---|---|---|---|---|---|---|---|---|---|
| | | 115 | | | | | 120 | | | | | 125 | | | |

| Leu | Gly | Ser | Ser | Phe | Phe | Ala | Gly | Thr | Val | Ile | Thr | Thr | Ile | Gly |
|---|---|---|---|---|---|---|---|---|---|---|---|---|---|---|
| 130 | | | | | 135 | | | | | 140 | | | | |

| Phe | Gly | Asn | Ile | Ser | Pro | Arg | Thr | Glu | Gly | Gly | Lys | Ile | Phe | Cys | Ile |
|---|---|---|---|---|---|---|---|---|---|---|---|---|---|---|---|
| 145 | | | | | 150 | | | | | 155 | | | | | 160 |

| Ile | Tyr | Ala | Leu | Leu | Gly | Ile | Pro | Leu | Phe | Gly | Phe | Leu | Leu | Ala | Gly |
|---|---|---|---|---|---|---|---|---|---|---|---|---|---|---|---|
| | | | | 165 | | | | | 170 | | | | | 175 | |

| Val | Gly | Asp | Gln | Leu | Gly | Thr | Ile | Phe | Gly | Lys | Gly | Ile | Ala | Lys | Val |
|---|---|---|---|---|---|---|---|---|---|---|---|---|---|---|---|
| | | | 180 | | | | | 185 | | | | | 190 | | |

| Glu | Asp | Thr | Phe | Ile | Lys | Trp | Asn | Val | Ser | Gln | Thr | Lys | Ile | Arg | Ile |
|---|---|---|---|---|---|---|---|---|---|---|---|---|---|---|---|
| | | 195 | | | | | 200 | | | | | 205 | | | |

| Ile | Ser | Thr | Ile | Ile | Phe | Ile | Leu | Phe | Gly | Cys | Val | Leu | Phe | Val | Ala |
|---|---|---|---|---|---|---|---|---|---|---|---|---|---|---|---|
| | 210 | | | | | 215 | | | | | 220 | | | | |

| Leu | Pro | Ala | Ile | Ile | Phe | Lys | His | Ile | Glu | Gly | Trp | Ser | Ala | Leu | Asp |
|---|---|---|---|---|---|---|---|---|---|---|---|---|---|---|---|
| 225 | | | | | 230 | | | | | 235 | | | | | 240 |

| Ala | Ile | Tyr | Phe | Val | Val | Ile | Thr | Leu | Thr | Thr | Ile | Gly | Phe | Gly | Asp |
|---|---|---|---|---|---|---|---|---|---|---|---|---|---|---|---|

-continued

```
                    245                 250                 255
Tyr Val Ala Gly Gly Ser Asp Ile Glu Tyr Leu Asp Phe Tyr Lys Pro
            260                 265                 270

Val Val Trp Phe Trp Ile Leu Val Gly Leu Ala Tyr Phe Ala Ala Val
        275                 280                 285

Leu Ser Met Ile Gly Asp Trp Leu Arg Val Ile Ser Lys Lys Thr Lys
    290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Leu Ser Val Glu Ile
            325                 330                 335

Tyr Asp Lys Phe Gln Arg Ala Thr Ser Ile Lys Arg Lys Leu Ser Ala
            340                 345                 350

Glu Leu Ala Gly Asn His Asn Gln Glu Leu Thr Pro Cys Arg Arg Thr
            355                 360                 365

Leu Ser Val Asn His Leu Thr Asn Glu Arg Asp Val Leu Pro Pro Leu
    370                 375                 380

Leu Lys Thr Glu Ser Ile Tyr Leu Asn Gly Leu Thr Pro His Cys Ala
385                 390                 395                 400

Gly Glu Glu Ile Ala Val Ile Glu Asn Ile Lys
            405                 410
```

<210> SEQ ID NO 19
<211> LENGTH: 398
<212> TYPE: PRT
<213> ORGANISM: Mus musculus

<400> SEQUENCE: 19

```
Met Arg Ser Thr Thr Leu Leu Ala Leu Leu Ala Leu Val Leu Leu Tyr
  1               5                  10                  15

Leu Val Ser Gly Ala Leu Val Phe Gln Ala Leu Glu Gln Pro His Glu
             20                  25                  30

Gln Gln Ala Gln Lys Lys Met Asp His Gly Arg Asp Gln Phe Leu Arg
         35                  40                  45

Asp His Pro Cys Val Ser Gln Lys Ser Leu Glu Asp Phe Ile Lys Leu
     50                  55                  60

Leu Val Glu Ala Leu Gly Gly Ala Asn Pro Glu Thr Ser Trp Thr
 65                  70                  75                  80

Asn Ser Ser Asn His Ser Ser Ala Trp Asn Leu Gly Ser Ala Phe Phe
                 85                  90                  95

Phe Ser Gly Thr Ile Ile Thr Thr Ile Gly Tyr Gly Asn Ile Val Leu
            100                 105                 110

His Thr Asp Ala Gly Arg Leu Phe Cys Ile Phe Tyr Ala Leu Val Gly
        115                 120                 125

Ile Pro Leu Phe Gly Met Leu Leu Ala Gly Val Gly Asp Arg Leu Gly
    130                 135                 140

Ser Ser Leu Arg Arg Gly Ile Gly His Ile Glu Ala Ile Phe Leu Lys
145                 150                 155                 160

Trp His Val Pro Pro Gly Leu Val Arg Ser Leu Ser Ala Val Leu Phe
                165                 170                 175

Leu Leu Ile Gly Cys Leu Leu Phe Val Leu Thr Pro Thr Phe Val Phe
            180                 185                 190

Ser Tyr Met Glu Ser Trp Ser Lys Leu Glu Ala Ile Tyr Phe Val Ile
        195                 200                 205
```

```
Val Thr Leu Thr Thr Val Gly Phe Gly Asp Tyr Val Pro Gly Asp Gly
    210                 215                 220
Thr Gly Gln Asn Ser Pro Ala Tyr Gln Pro Leu Val Trp Phe Trp Ile
225                 230                 235                 240
Leu Phe Gly Leu Ala Tyr Phe Ala Ser Val Leu Thr Thr Ile Gly Asn
                245                 250                 255
Trp Leu Arg Ala Val Ser Arg Arg Thr Arg Ala Glu Met Gly Gly Leu
            260                 265                 270
Thr Ala Gln Ala Ala Ser Trp Thr Gly Thr Val Thr Ala Arg Val Thr
        275                 280                 285
Gln Arg Thr Gly Pro Ser Ala Pro Pro Glu Lys Glu Gln Pro Leu
    290                 295                 300
Leu Pro Ser Ser Leu Pro Ala Pro Ala Val Val Glu Pro Ala Gly
305                 310                 315                 320
Arg Pro Gly Ser Pro Ala Pro Ala Glu Lys Val Glu Thr Pro Ser Pro
                325                 330                 335
Pro Thr Ala Ser Ala Leu Asp Tyr Pro Ser Glu Asn Leu Ala Phe Ile
                340                 345                 350
Asp Glu Ser Ser Asp Thr Gln Ser Glu Arg Gly Cys Ala Leu Pro Arg
            355                 360                 365
Ala Pro Arg Gly Arg Arg Pro Asn Pro Ser Lys Lys Pro Ser Arg
    370                 375                 380
Pro Arg Gly Pro Gly Arg Leu Arg Asp Lys Ala Val Pro Val
385                 390                 395
```

<210> SEQ ID NO 20
<211> LENGTH: 15
<212> TYPE: DNA
<213> ORGANISM: Homo sapiens

<400> SEQUENCE: 20
accctgactc ctcag                                                          15

<210> SEQ ID NO 21
<211> LENGTH: 15
<212> TYPE: DNA
<213> ORGANISM: Homo sapiens

<400> SEQUENCE: 21
tccctttctt tgcag                                                          15

<210> SEQ ID NO 22
<211> LENGTH: 15
<212> TYPE: DNA
<213> ORGANISM: Homo sapiens

<400> SEQUENCE: 22
catatttctc accag                                                          15

<210> SEQ ID NO 23
<211> LENGTH: 15
<212> TYPE: DNA
<213> ORGANISM: Homo sapiens

<400> SEQUENCE: 23
ctttgctctt cctag                                                          15

<210> SEQ ID NO 24
<211> LENGTH: 15

```
<212> TYPE: DNA
<213> ORGANISM: Homo sapiens

<400> SEQUENCE: 24
tttggttgtt ttcag                                              15

<210> SEQ ID NO 25
<211> LENGTH: 15
<212> TYPE: DNA
<213> ORGANISM: Homo sapiens

<400> SEQUENCE: 25
ctgtctcttg gccag                                              15
```

HUMAN TREK2, A STRETCH- AND ARACHIDONIC ACID-SENSITIVE K+ CHANNEL ACTIVATED BY INHALATIONAL ANESTHETICS AND NILUZOLE

CROSS-REFERENCE TO RELATED APPLICATION

This application is related to U.S. Provisional Application No. 60/214,559, filed on Jun. 27, 2000, and claims the benefit of that earlier filing date. Provisional Application No. 60/214,559 is hereby incorporated by reference in its entirety.

FIELD OF THE INVENTION

This invention relates to DNA and peptide sequence of TREK2, a novel mammal member of the family of potassium ($K^+$) channels with two pore domains. The invention also provides the use of this channel in methods for screening various bioactive compounds, in particular, those having anesthetic properties.

BACKGROUND

Potassium channel subunits containing two pore domains ("K 2P channels") form a novel class of background $K^+$ channels. These K 2P channels have unique pharmacological and functional properties (1–10). They are active at all membrane potentials and display very rapid kinetics of activation and deactivation, and no inactivation. Their widespread tissue distribution suggests that one of their major physiological roles is setting the resting membrane potential in many different cell types. Background $K^+$ channels with specific functional and regulatory properties, as well as unique tissue distribution, have now been cloned. These channels could be involved in more specific functions such as epithelial $K^+$ transport and regulation of neuronal and muscular excitability (11).

Various $K^+$ currents have been recorded in vivo from neuronal, cardiac and smooth muscle cells, that form a subfamily of background $K^+$ currents sensitive to fatty acids (12–15). Recently, fatty acid-activated $K^+$ channels have been cloned from mice and humans (2, 6, 16). These channels named TREK1 (TWIK-Related $K^+$ channel) and TRAAK (TWIK-Related Arachidonic Acid-stimulated $K^+$ channel) produce quasi-instantaneous currents that are outwardly rectifying in physiological $K^+$ gradient. These channels have a low basal activity compared to TASK background channels (3–5). However, they can be strongly activated by application of arachidonic acid. This effect is specific for unsaturated fatty acids.

Oleate, linoleate, eicosapentaenoate and docosahexaenoate all strongly activate TREK1 and TRAAK, while saturated fatty acids such as palmitate, stearate and arachidate are ineffective (6, 17). Another efficient way for activating these channels is the application of a stretch to the cell membrane (17, 18). Both channels are activated by shear stress, cell swelling and negative pressure. They are mechano-sensitive $K^+$ channels.

Compared to TRAAK, TREK1 has additional features. TREK1 is inhibited by activators of protein kinases C and A (PKC, PKA). The site for PKA phosphorylation has been localized in the cytoplasmic carboxy-terminal part of the channel (17). TREK1 but not TRAAK is opened by internal acidification (19). Lowering pHi shifts the pressure-activation relationships toward positive values and leads to channel opening at atmospheric pressure. TREK1, but not TRAAK, is activated by inhalational general anesthetics, halothane and isoflurane, at concentrations used in human general anesthesia (16). Finally, TREK1 and TRAAK have different tissue distributions, the expression of TRAAK being more restricted to neuronal cells than TREK1 (2, 6, 20).

This invention describes the cloning, the genomic organization, the localization and the functional characterization of a novel human $K^+$ channel with two pore domains. The molecular and functional properties of this channel indicate that it too belongs to the particular subclass of mechano-sensitive and unsaturated fatty acid-activated $K^+$ channels. TREK2 is more related to TREK1 than to TRAAK, and like TREK1, it is activated by general anesthetics at clinical concentrations. Moreover, TREK2 is modulated by different types of neurotransmitter receptors. In high symmetrical $K^+$ conditions, TREK2 produces currents whose current-voltage relationship is weakly inwardly rectifying.

SUMMARY OF THE INVENTION

Accordingly, the invention provides a protein comprising a mammalian $K^+$ channel with two pore domains that produces currents whose current-voltage relationship is weakly inwardly rectifying in high symmetrical $K^+$ conditions. The invention provides more particularly a human $K^+$ channel with two pore domains that produces currents whose current-voltage relationship is weakly inwardly rectifying in high symmetrical $K^+$ conditions. In a preferred embodiment, the human $K^+$ channel with two pore domains of the invention comprises the sequence of amino acids in SEQ ID No. 2.

The invention provides a nucleic acid molecule comprising a nucleic acid sequence coding for a mammalian $K^+$ channel with two pore domains that produces currents whose current-voltage relationship is weakly inwardly rectifying in high symmetrical $K^+$ conditions or a nucleic acid sequence coding for a fragment of such a mammalian $K^+$ channel. The invention also provides a nucleic acid molecule comprising a nucleic acid coding sequence for a human $K^+$ channel with two pore domains that produces currents whose current-voltage relationship is weakly inwardly rectifying in high symmetrical $K^+$ conditions or for a fragment of such a protein. In a preferred embodiment, the invention provides a nucleic acid molecule which encodes a human $K^+$ channel with two pore domains that produces currents whose current-voltage relationship is weakly inwardly rectifying in high symmetrical $K^+$ conditions or for a fragment of this protein, whose amino acid sequence is represented in SEQ ID No. 2. In another embodiment, the amino acid sequence of nucleic acid molecule comprises SEQ ID No. 1.

Moreover, in other embodiments, the invention contemplates nucleotide sequences derived from the above sequences, for example, from the degeneracy of the genetic code, and which encode for proteins presenting characteristics and properties of a mammalian $K^+$ channel with two pore domains whose current-voltage relationship is weakly inwardly rectifying in high symmetrical $K^+$ conditions.

Another aspect of the invention provides polyclonal or monoclonal antibodies directed against a mammalian $K^+$ channel whose current-voltage relationship is weakly inwardly rectifying in high symmetrical $K^+$ conditions, or a derivative or a fragment thereof. These antibodies can be prepared by the methods known in the art and described in the literature. Accordingly, polyclonal antibodies are prepared by injecting into animals proteins which have been extracted from the epithelium or produced by genetic transformation of a host, and recovering antiserums and antibodies from the antiserums by, for example, affinity chromatography. Monoclonal antibodies can be produced by fusing myeloma cells with spleen cells from animals previously immunized using the receptors of the invention. These antibodies are useful for screening for a novel mammalian $K^+$ channel with two pore domains or in the search for the human TREK2 channel homologues in other mammals.

The invention also provides a integration and expression vector comprising at least one nucleic acid molecule described above, operably associated with adapted control sequences at the 5' and 3' ends, useful in transforming cellular hosts and expressing in a cellular hosts a mammalian $K^+$ channel with two pore domains that produces currents whose current-voltage relationship is weakly inwardly rectifying in high symmetrical $K^+$ conditions of the invention or a fragment thereof. The preparation of these vectors as well as the production or expression in a protein host of the invention can be carried out by molecular biology and genetic engineering techniques well known in the art.

A nucleic acid molecule coding for a mammalian $K^+$ channel with two pore domains that produces currents whose current-voltage relationship is weakly inwardly rectifying in high symmetrical $K^+$ conditions or a vector according to the invention can be used to transform cellular hosts, animals and to establish a line of transgenic cellular hosts or animals. The vector used is chosen to function in the host into which it is to be transferred; it can be any vector such as a plasmid. Thus the invention also relates to cellular hosts expressing a mammalian $K^+$ channel with two pore domains whose current-voltage relationship is weakly inwardly rectifying in high symmetrical $K^+$ conditions obtained in conformity with the preceding processes.

The invention also relates to nucleic and oligonucleotide probes prepared from the molecules of nucleic acid according to the invention. These probes, marked advantageously, are useful for hybridisation detection of similar mammalian $K^+$ channel with two pore domains that produces currents whose current-voltage relationship is weakly inwardly rectifying in high symmetrical $K^+$ conditions in other individuals or species. As tools for such hybridization detection, these probes are put into contact with a biological sample. Different hybridisation techniques can be used, such as Dot-blot hybridisation or replica hybridisation (Southern technique) or other techniques (DNA chips). Such probes make it possible to detect similar sequences quickly in the encoding genes for mammalian $K^+$ channel which allows screening of the presence, origin and preservation of these proteins. The oligonucleotide probes are useful for PCR protocols with a diagnostic aim, or to search for genes in other species.

TREK2 is activated by general anesthetics at clinical concentrations. Consequently, this invention is also useful in the pharmaceuticals field in methods for identifying biologically active compounds with anesthetics properties. Accordingly, the invention also provides a method for identifying a biologically active compound with anesthetics properties comprising:

providing a biologically active compound;
contacting said compound with a cellular host expressing on its surface a mammalian $K^+$ channel with two pore domains that produces currents whose current-voltage relationship is weakly inwardly rectifying in high symmetrical $K^+$ conditions;
determining the $K^+$ transport activity of said mammalian $K^+$ channel; and
selecting the compound capable of activating $K^+$ transport as indicative of said compound having anesthetics properties.

This method is advantageously realised with a human $K^+$ channel with two pore domains that produces currents whose current-voltage relationship is weakly inwardly rectifying in high symmetrical $K^+$ conditions and more preferably with a human $K^+$ channel comprising the sequence of amino acids in SEQ ID No. 2. The methods of the invention can be carried out with cellular hosts which transiently or constitutively express on their surface the mammalian $K^+$ channel of the invention. The cellular host may be of any type which can express the protein in appropriate conformation to allow for the $K^+$ transport. Examples of such cellular hosts include mammalian cells, vertebrate cells and invertebrate cells.

The invention additionally provides pharmaceutical compositions containing a biologically active compound with anesthetics properties identified by a method described above.

Other advantages and characteristics of the invention will become apparent by reading the examples herein concerning the cloning, genomic organization, chromosomal mapping, tissue distribution, and heterologous expression of human TREK2

BRIEF DESCRIPTION OF THE DRAWINGS

FIG. 1A shows the amino acid alignment of TREK2 [SEQ ID NO: 2], TREK1 [SEQ ID NO: 18] and TRAAK [SEQ ID NO: 19] channels. Relative positions of introns are indicated by arrows. M1 to M4 membrane-spanning segments and P1 and P2 pore-domains are indicated. The star shows the point of divergence between the TREK2 channel sequences from rat and human.

FIG. 1B shows the sequences at the boundaries by exon-intron. Exonic sequence is in upper case. The sizes of introns is indicated.

FIG. 1C show a dendrogram of K 2P channels cloned in human established with ClustalW and Treeview.

FIG. 2A is a Southern blot of tissue distribution analysis by RT-PCR. The amplified products were analyzed by Southern blot using specific internal primers as probes. To check the integrity of cDNAs, a GAPDH fragment was amplified. sk. muscle, skeletal muscle; sm intestine, small intestine; PBL, Peripheral Blood Leukocytes.

FIG. 2B is a Northern blot of TREK2 localization in the brain. Blots were hybridized at high stringency with specific probes. Each lane contains 2 $\mu$g of poly (A)+RNA.

FIG. 3A is a graphic depiction of the biophysical properties of TREK2 currents in whole-cell configuration. Superimposed current traces elicited by voltage steps from −150 mV to +70 mV by increments of 20 mV.

FIG. 3B is a graphic depiction of the current-voltage (I-V) relationships in physiological (5 mM $K^+$) and symmetrical (150 mM $K^+$) $K^+$ gradients (800-ms voltage ramps from −130 mV to +100 mV from a holding potential of −80 mV).

FIG. 3C shows the steady-state single-channel activities at the indicated potentials. Outside-out patch mode in physiological (left traces) and symmetrical (right traces) $K^+$ conditions.

FIG. 3D shows the single-channel I-V curves of TREK2 obtained from outside-out patches in physiological (filled square) and symmetrical (open circle) K$^+$ conditions. Mean of five examined patches. Single-channel conductance was 128 pS at −40 mV and 100 pS at +40 mV when measured in symmetrical K$^+$ conditions.

FIG. 4A shows the reversible activation of TREK2 by membrane stretch in an inside-out patch exhibiting a low basal activity at +50 mV. The control value of pHi was 7.3.

FIG. 4B shows the effects of increasing stretch stimulation (in mmHg) on TREK2 activation in a multi-channel inside-out patch held at 0 mV. The control value of pHi was 7.3.

FIG. 4C shows the effects of membrane voltage (as indicated) on TREK2 activation by the same membrane stretch (−75 mmHg) from multi-channel inside-out patch.

FIG. 4D shows the reversible activation of TREK2 by internal acidosis (pHi 5.6) in a patch displaying a low basal activity. The maximum TREK2 activation is obtained in depolarized conditions.

FIG. 4E shows the voltage-dependence of activation by internal acidosis at pH 5 from multi-channel inside-out patch.

FIG. 5A is a graphic depiction of halothane (1 mM) stimulating TREK2 channel activity elicited in the whole-cell configuration. The I-V curves were obtained with a voltage-ramp protocol of 800 ms duration starting from a holding potential of −80 mV.

FIG. 5B is a bar chart representation of the activation of TREK-2 channel activity by chloroform (CHCl3), isoflurane (Iso) and halothane. Number of cells in each experimental condition is indicated above bar.

FIG. 5C shows the transient activation of TREK2 by riluzole. Evolution of the current under control conditions (1), after a 20 s application of riluzole (2), after a 3 min application of riluzole (3) and after a 1 min wash (4). The voltage-clamp protocol consists of the same ramp as in A applied every 10 s. The current was monitored at +100 mV.

FIG. 5D is a graphic depiction of the corresponding I-V curves of the experiment shown in 5C.

FIG. 6A is a graphic depiction of the activation by arachidonic acid (AA) of the whole-cell TREK2 current. The I-V curves were obtained with a voltage-ramp protocol of 800 ms duration starting from a holding potential of −80 mV.

FIG. 6B is a graphic depiction of the activation by lysophosphatidylcholine (LPC). The same protocol as in FIG. 6A was followed.

FIG. 6C is a bar chart of the effect of fatty acids on TREK2. AA, arachidonic acid, DHA, docosahexaenoic acid, LA, linoleic acid, PA, palmitic acid, LPC, lysophosphatidylcholine.

FIG. 6D is a graphic depiction of the regulation of TREK2 channel activity by cAMP. Inhibition of the current after external application of 500 μM CPT-cAMP. The same voltage protocol as in FIG. 6A were followed.

FIG. 7A shows TRK2 co-expressed together with 5HT4sR the receptor. The receptor was activated by application of 5-hydroxytryptamine (5-HT).

FIG. 7B shows TRK2 co-expressed together with mGluR2 the receptor. The receptor was activated by glutamate.

FIG. 7C shows TRK2 co-expressed together with the mGluR1 receptor. The receptor was activated by glutamate. For FIGS. 7A–7C, the left side shows the evolution of the whole-cell TREK2 current under control conditions (1), at the steady-state effect after receptor activation (2) and after wash (3). The voltage-clamp protocol consists of a voltage-ramp of 800 ms duration starting from a holding potential of −80 mV applied every 10 s. The current was monitored at +100 mV. The right side shows the corresponding I–V curves of the experiments shown on the left side. No effect on TREK2 current was seen after 5-HT and glutamate applications on COS cells transfected with only TREK2.

DETAILED DESCRIPTION

Figure 1:
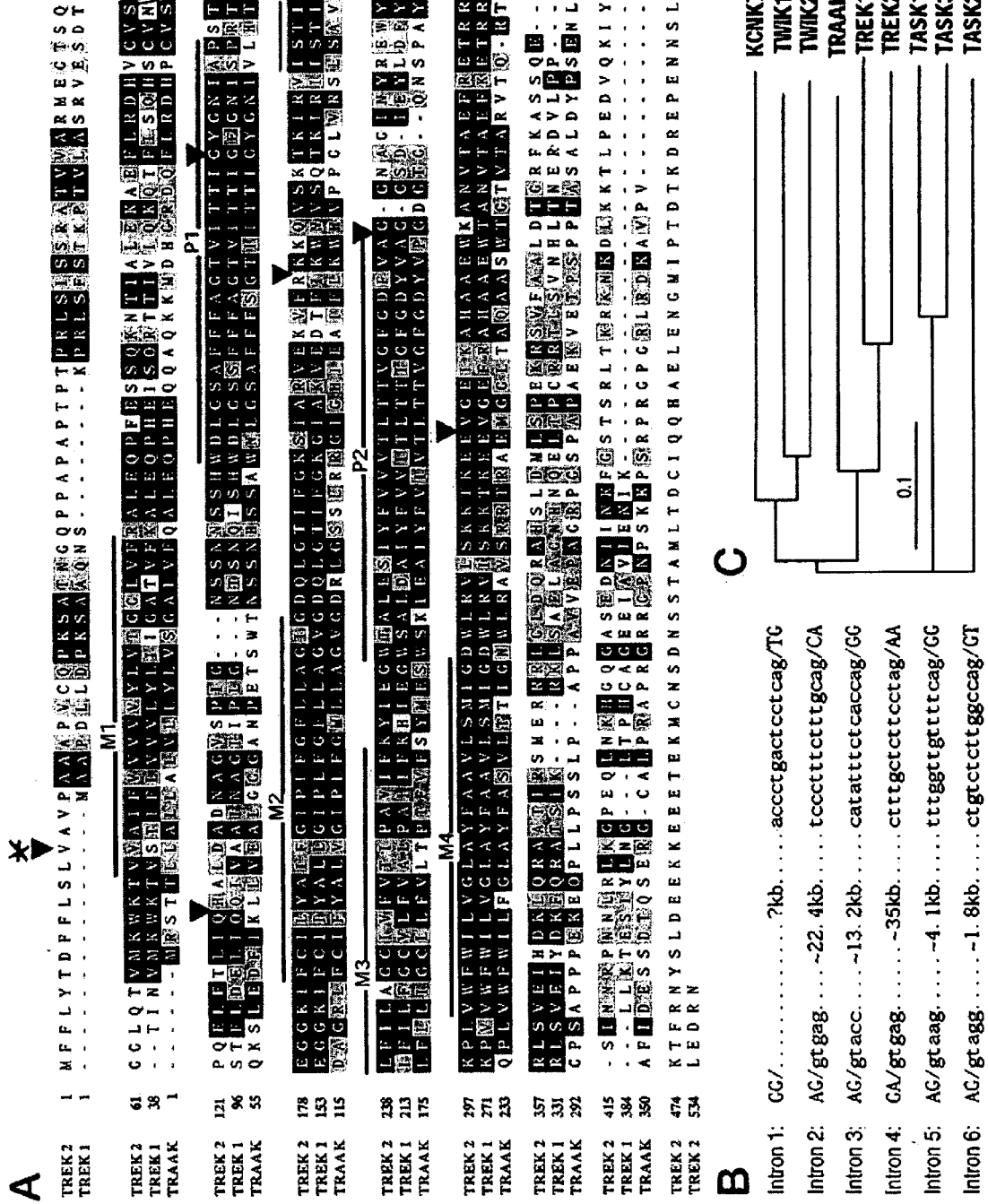
FIG. 1 shows the sequence and genomic organization of TREK2.

TREK2 is a novel member of the fatty acid-activated and mechanosensitive K$^+$ channel family that includes TREK1 and TRAAK. Like these channels, TREK2 is not blocked by TEA and Ba 2+ and is stimulated by polyunsaturated fatty acids such as arachidonic, docosahexanoic and linoleic acids, by lysophospholipids and by application of a negative pressure to the cell membrane. In addition, TREK2 shares with these channels the same gene organization indicating that the three genes probably derive from a common ancestral gene. However, TREK2 is more related to TREK1 than to TRAAK. TREK2 and TREK1 have unique functional and pharmacological properties which are not shared by TRAAK: they are negatively regulated by agents that activate PKA, they are positively regulated by acidification of internal medium and they are strongly activated by volatile general anesthetics. Like TREK1, TREK2 is also transiently activated by riluzole while TRAAK is permanently activated. For TREK1, the inhibition that follows activation by riluzole has been related to an increase of intracellular cAMP and a consequent inhibitory PKA-phosphorylation of the channel (30). In molecular terms, TREK2 is also more related to TREK1, not only if considering the overall sequence homology, but also the distribution of this homology along the sequences. TRAAK, TREK1 and TREK2 have a conserved domain that extends from M1 to M4. Between TREK1 and TREK2, the homology level remains high after M4 and continues over 50 residues. This post-M4 carboxy terminal part is crucial for TREK1 channel sensitivity not only to fatty acids and stretch but also to PKA and pHi (17, 16, 19). The high level of conservation in this domain between TREK1 and TREK2 explains why these channels have closely related mechanisms of regulation.

Interestingly, the PKA site which is implicated in the negative regulation by phosphorylation of TREK1 (17) is conserved in TREK2 (serine 359) suggesting that TREK2 is negatively regulated by PKA in the same way as TREK1. In TREK1, the cytoplasmic amino terminus is not important for the channel activity and for its mechanical and chemical regulations (17, 16, 19). This is also the case for TREK2 because a truncated TREK2 beginning at methionine 55 apparently conserves its properties after the removal of the first 54 residues by mutagenesis (not shown).

The cloning of a novel channel from rat has been published on-line (32). This channel is clearly the rat ortholog of human TREK2. These channels have a similar tissue distribution although TREK2 is not expressed in the rat kidney while it is highly expressed in the human kidney. In addition, they share many common functional properties such as single channel conductance and sensitivity to polyunsaturated fatty acids and stretch. However, despite a high sequence identity (more than 70%), the cytoplasmic amino-terminal part encoded by the first exon (as shown in FIG. 1A) is clearly unrelated between these two channels suggesting alternative splicing from a single gene.

The Physiological Role of TREK2

Several arachidonic acid-activated and mechanosensitive $K^+$ currents have been characterized (15) in neurons cultured from mesencephalic and hypothalamic areas of the rat brain. Their functional properties are similar to the properties of TREK-related channels.

Three different native currents have been identified in neurons with I-V relationships being weakly outwardly rectifying or linear or weakly inwardly rectifying, in high symmetrical $K^+$ conditions. Under the same conditions, the I-V relationship of TREK1 is weakly outwardly rectifying and the I-V relationship of TRAAK is linear. These results, together with the fact that TREK1 and TRAAK are expressed in brain areas that contain neurons expressing the native currents, suggested that both cloned channels contribute to these native currents. None of the channels cloned until now corresponded to the third type of current with an inward rectification. From the Northern blot analysis, it appears that TREK2 is expressed in the same brain areas as TREK1. Since TREK2 produces currents whose I-V relationship is weakly inwardly rectifying, we propose that TREK2 forms or contributes to the formation of this third type of native arachidonic acid-activated and mechanosensitive current with inward rectification. These channels are expected to play a role in the control of neuronal excitability and particularly, in the control of the resting membrane potential, if they are active at rest in vivo.

The level of TREK2 activity can be regulated by the three different types of G-protein coupled receptors. This indicates that TREK2 activity in neurons is fine-tuned by a variety of neurotransmitters and that TREK2 could play a role similar to the role of the K 2P channel TASK1. In cerebellar granule cells and hypoglossal motoneurons, TASK1 has a central importance in controlling cell excitability and the modulation of its activity by a variety of neurotransmitters acting via Gq-coupled receptors profoundly alters both resting membrane potential and excitability (33, 34). It is interesting to note that the signal transduction pathway by which Gq-coupled receptor inhibits TASK1 does not involve PKC or Ca 2+ (33, 34) as also observed for TREK2. A major difference between TASK1 and TREK2 is that TREK2 is also regulated via Gi- and Gs-coupled receptors. TREK2 probably plays an important role in charge of tuning neuronal excitability in response to a variety of neurotransmitters and hormones. The isolation and the characterization of TREK2 constitute an additional step toward the understanding of this particular class of $K^+$ channels which probably plays a wide variety of important physiological roles in the brain and other tissues (11). Furthermore, because TREK2 is a target of volatile anesthetics ((16) and this patent application) and riluzole, a neuroprotective drug (6, 30), it has an important impact in medicine. The ability of anesthetics to activate the K+ transport provide a basis for identification of bioactive compounds which have anesthetic properties.

This invention is further exemplified by the following illustrative and non-limiting example.

EXAMPLE

Cloning of TREK2

Sequences of two P domain $K^+$ channels were used to search homologs in public DNA databases by using the tBlastn alignment program and TREK1 as the query sequence (21). This led to the identification of a genomic sequence (EMBL accession number AL133279.1) which showed significant similarities with TREK1. In order to characterize the corresponding full-length cDNA, 5'- and 3'-rapid amplifications of cDNA ends (RACE PCR) were performed on adult human brain cDNAs ligated with adaptors (22). Two antisense primers for 5'-RACE (5'-ACTGCCGAGGTCCCAGTGGCTGCTGTT- 3' [SEQ ID No. 3] and 5'-TCTGGCTGCTCTCAAAGGGCTGCT-3' [SEQ ID No. 4]) and two sense primers for 3'-RACE (5'-GACGATCCCTGCTGTCATCTT-3' [SEQ ID No. 5] and 5'-TTGCAGCTGTCCTCAGTAGATCG-3' [SEQ ID No. 6]) were derived from genomic sequences.

Two successive RACE reactions were performed by using anchor primers 5'-TAGAATCGAGGTCGACGGTATC-3' [SEQ ID No. 7] and 5'-GATTTAGGTGACACTATAGAATCGA-3' [SEQ ID No. 8]. The amplified products were subcloned into pGEMt easy (Promega) and eight clones of each product were sequenced (Applied Biosystems model 373A). The entire coding sequence was amplified from human brain cDNA by PCR using a low-error rate DNA polymerase and then subcloned into the pIRES-CD8 vector to give pIRES-CD8. TREK2. Inserts from two different independent PCR-ligation experiments were sequenced on both strands and found to be identical.

Analysis of TREK1, TREK2 and TRAAK Distributions

For RT-PCR experiment, Multiple Tissue cDNA panels were used as template according to the manufacturer's protocol (Clontech). Primers were: TREK2, sense primer 5'-CAGCCCTTTGAGAGCAGCC-3' [SEQ ID No. 9], antisense primer 5'-AAGATGACAGCAGGGATCGTC-3' [SEQ ID No. 10], TRAAK, 5'-GAGGCCCGGCCAGGGGATCCTG-3' [SEQ ID No. 11] and 5'-CTCAGTGCTCACCACCATCG-3' [SEQ ID No. 12], and TREK1, 5'-GGATTTGGAAACATCTCACCACGCACA-3' [SEQ ID No. 13] and 5'-GATCCACCTGCAACGTAGTC-3' [SEQ ID No. 14]. PCR conditions were 32 cycles of 30 s at 94° C., 30 s at 55° C., and 30 s at 72° C. PCR products were separated by electrophoresis, transferred onto nylon membranes, and probed with 32 P-labeled primers (TREK2, 5'-ACTGCCGAGGTCCCAGTGGCTGCTGTT-3' [SEQ ID No. 15]; TRAAK, 5'-TCAGGCTG CCAGCTGGACTG-3' [SEQ ID No. 16]; TREK1, 5'-TAGCTGATCTCCAACTCCAGCCAAG-3' [SEQ ID No. 17]). For Northern blot analysis, multiple tissue Northern blots from Clontech were probed with the $^{32}$P-labeled insert of pIRES-CD8. TREK2 in Ultrahyb hybridization buffer (Ambion) at 50° C. for 18 h then washed stepwise at 55° C. to a final stringency of 0.2×SSC, 0.3% SDS. Blots were then dehybridized according the manufacturer's protocol and reprobed with TREK1 and TRAAK following the same procedure. A 0.7 kb BamHI fragment from pCD8. hTREK1 and the insert from pIRES-CD8. hTRAAK were used as probes. Autoradiograms were exposed 24 h at −70° C. on BioMax films by using a Transcreen-HE Intensifying Screen (Kodak).

Electrophysiology in Transfected COS Cells.

COS cells were seeded at a density of 20,000 cells per 35 mm dish, 24 h prior transfection. Cells were transiently transfected by the classical DEAE-dextran method with 0.2

µg of pIRES-CD8. TREK2 with or without mGluR1, mGluR2 or 5HT4sR expression vectors (a generous gift of Drs J P Pin and A Dumuis, Montpellier, France).

Transfected cells were visualized 48 h after transfection using the anti-CD8 antibody-coated beads method. For whole-cell experiments, the patch electrode solution (INT) contained 150 mM KCl, 3 mM $MgCl_2$, 5 mM EGTA and 10 mM HEPES, adjusted to pH 7.3 with KOH; the external solution (EXT) contained 150 mM NaCl, 5 mM KCl, 3 mM $MgCl_2$, 1 mM $CaCl_2$ and 10 mM HEPES, adjusted to pH 7.4 with NaOH. For outside-out patch recordings, the pipette solution was the INT solution and the external solution was either the EXT solution (5 mM $K^+$) or a $K^+$-rich EXT solution which contained 150 mM KCl instead of 150 mM NaCl.

For inside-out patch recordings, pipettes were filled with the EXT solution and the bathing solution was the INT solution buffered either at pH 7.3 or at pH 5.6 in the internal acidosis experiments. Cells were continuously superfused with a microperfusion system during the experiment (0.2 ml per min) done at room temperature. A RK400 patch-clamp amplifier was used for whole-cell and single-channel recordings (Bio-Logic, Claix, France). Single-channel data were low-pass filtered at 5 KHz and digitized at 50 KHz using a DAT recorder (Bio-Logic, Claix, France). pClamp software was used to analyze whole-cell data and Biopatch software (Bio-Logic) to analyze single-channel data.

Concentrations of volatile anesthetics were adjusted from saturated solutions (isoflurane, 15.3 mM; halothane, 17.5 mM and chloroform, 66.6 mM) in saline at room temperature (16). Mechanical stimulation was applied through an open loop pressure generating system and monitored at the level of the patch pipette by a calibrated pressure sensor (17).

Molecular Cloning of TREK2

DNA sequences produced in the frame of the human genome sequencing program are rapidly accumulating in the public high-throughput-genomic-sequences (HTGS) database. Searches of this database using the Blast sequence alignment program (21) led to the identification of human sequences restrained to a single genomic contig. The analysis of these sequences suggested the presence of introns and exons forming a gene coding for a novel K 2P subunit. Oligonucleotides were deduced from the potential exon sequences and used to clone cDNA fragments from human brain by using Rapid Amplification of CDNA Ends (RACE)-PCR. The sequence deduced from these cDNAs is 2730 bp long and contains an open reading frame (ORF) of 1617 nucleotides predicting a 538 amino acids polypeptide (as shown in FIG. 1A). This protein has the same overall structure than the previously cloned K 2P subunits. It displays four membrane spanning segments (M1 to M4), two P domains (P1 and P2) and an extended loop between M1 and P1. The dendrogram shown in FIG. 1C clearly indicates that this subunit is more related to TREK1 and TRAAK than to other K 2P subunits. Therefore, this novel K 2P subunit was named TREK2 (gene KCNK10 in the human genome organization (HUGO) nomenclature). TREK2 shares 63% identity and 78% homology with TREK1. The homology level falls to 69% with TRAAK and to 50-55% with the other K 2P subunits.

TREK2 Gene Organization and Location

The genomic organization of TREK2 was deduced from the alignment of the cloned cDNAs with the genomic sequences available in the HTGS DNA database. The ORF is composed of six introns and seven exons. The amino-terminus of TREK2 is encoded by exon 1, the M1 domain by exon 2, M2 by exon 4, M3 by exon 5 and M4 by exon 6. The third exon codes for the carboxy-terminal part of the M1P1 interdomain and the seventh one encodes the large carboxy-terminus of the channel (as shown in FIG. 1A). The length of introns 2–6 varies from 1.8 kb to 35 kb (as shown in FIG. 1B). The first exon being out of the genomic contig, the size of the first intron is not known. At this point, it cannot be excluded that the 5' untranslated sequence corresponds to more than one exon.

This organization is different of TWIK1 and TASK3 gene organizations. TWIK1 contains three exons separated by two large introns (23) and TASK3 contains only one short intron (10). However, genomic organization of TREK2 is very close to the genomic organization of both TRAAK (24) and TREK1 channels (unpublished results) genomic organizations. Introns 2 to 6 are found in the same positions. This observation confirms that these three channels are closely related and suggests that they have arisen by gene duplication from a common ancestor. A particular feature found in TWIK1, TASK1, TREK1, TREK2, TRAAK, TASK2 and TASK3 genes is the presence of a conserved intron in the sequence coding the P1 domain (third intron in the TREK2 gene). The intron site is between the first and the second nucleotides of the codon coding for the first glycine residue of the pore signature sequence G-Y/F/L-G. An intron in the same position is found in 20 genes among the 36 examined that encode potential K 2P channels in the nematode *Caenorhabditis Elegans* (25) and in 8 genes among 11 in the Drosophila as determined by analyzing its recently released genomic sequences. The significance of this conserved intron position is not known, however it is worth noting that this intron has been conserved in mammals where it might eventually have the same role as in the nematode. The analysis of genomic contig bearing the TREK2 gene showed that this sequence contains two Sequence Tag Sites (STS), D14S1058 and WI-6710. WI-6710 has been placed on the WICGR radiation hybrid map 308.53 cR from top of Chr14 linkage group and D14S1058 has been mapped by Genethon 86.3 cM from top of Chr14 linkage group. These results are in agreement and indicate that the chromosomal location of TREK2 gene is 14q31. This location is different from those of TREK1 (1q41) (26) and TRAAK (11q13) (24).

Tissue Distribution of TREK2

Figure 2:
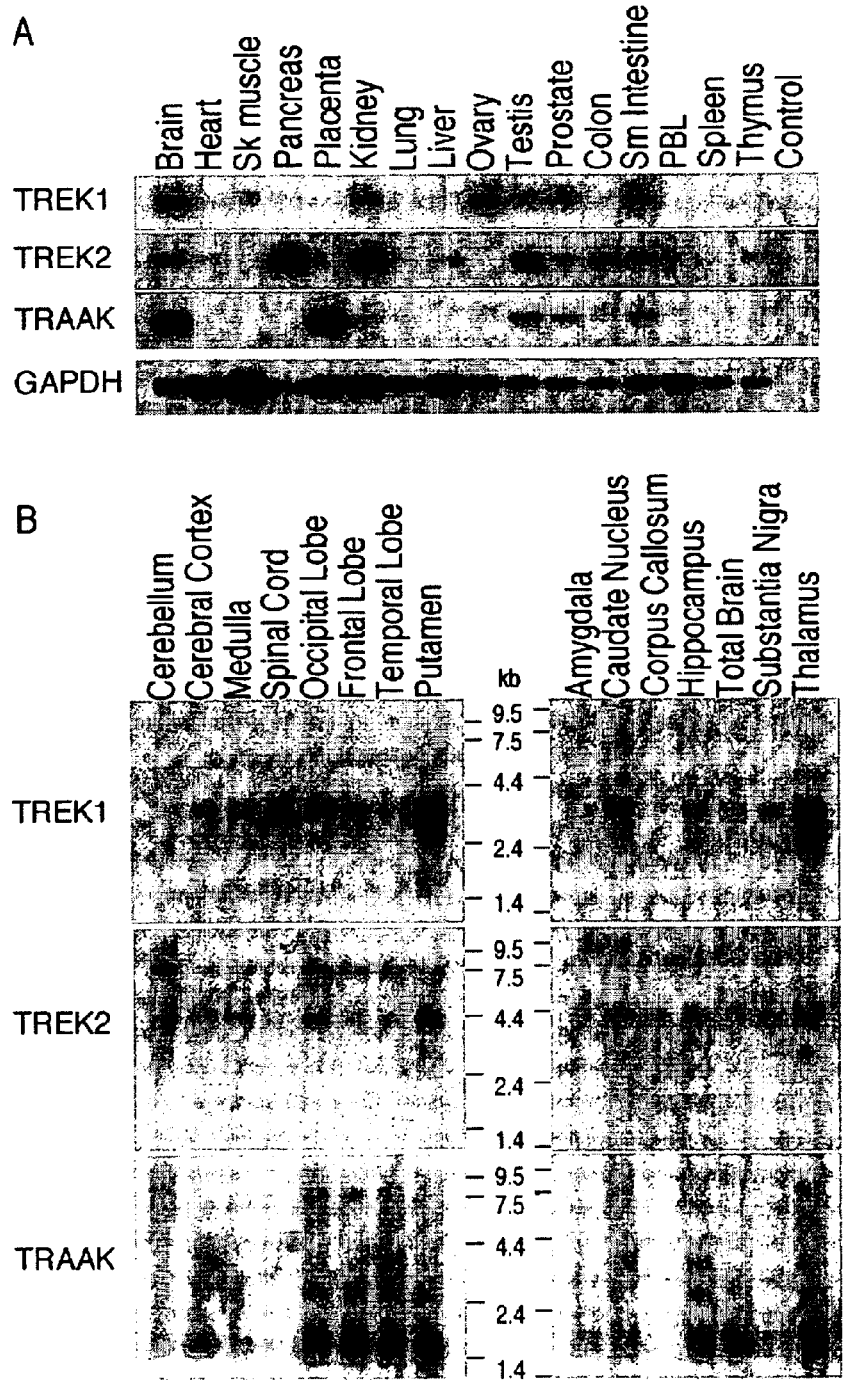
FIG. 2 shows pictures of gel electrophoresis results showing the expression of TREK2 in adult human tissue.

The expression of TREK2 in various adult human tissues was examined by RT-PCR analysis. As shown in FIG. 2A, TREK2 is abundantly expressed in kidney and pancreas, and more moderately in testis, brain, colon and small intestine. Only very faint signals were obtained in liver, heart, prostate and thymus. This expression pattern contrasts with the TREK1 and TRAAK tissue distributions (as shown in FIG. 2A). Some tissues express only one of these channels: for instance, pancreas and colon (TREK2), placenta (TRAAK) and ovary (TREK1). Other tissues do not express these channels or only to modest levels: heart, skeletal muscle, lung, PBL and spleen. Finally, some tissues express two or three of these related channels: brain, testis and small intestine. Distributions of TREK1, TREK2 and TRAAK in the different areas of the human brain were analyzed by Northern blot. As shown in FIG. 2B, the TREK2 probe detected two transcripts of 4 and 7.5 kb. TREK2 is mainly expressed in cerebellum, occipital lobe, putamen and thalamus and to lower levels in the other examined areas. No expression was detected in amygdala and spinal cord. The 4 kb transcript is expressed at a higher level than the 7.5 kb transcript except in occipital lobe and cerebellum. As expected from the previous studies on TREK1 and TRAAK expression in rodent central nervous system (2, 6, 20), these two channels have a widespread distribution in the human brain. The 2 kb TRAAK transcript and the 2.7 and 3.3 kb TREK1 transcripts are well expressed in areas where TREK2 is mainly expressed: putamen and thalamus. In the brain cortex (occipital, frontal and temporal lobes), TRAAK is also highly expressed. Finally, TREK1 is the only channel of this family to be expressed in the spinal cord.

Biophysical Properties of TREK2

Figure 3:
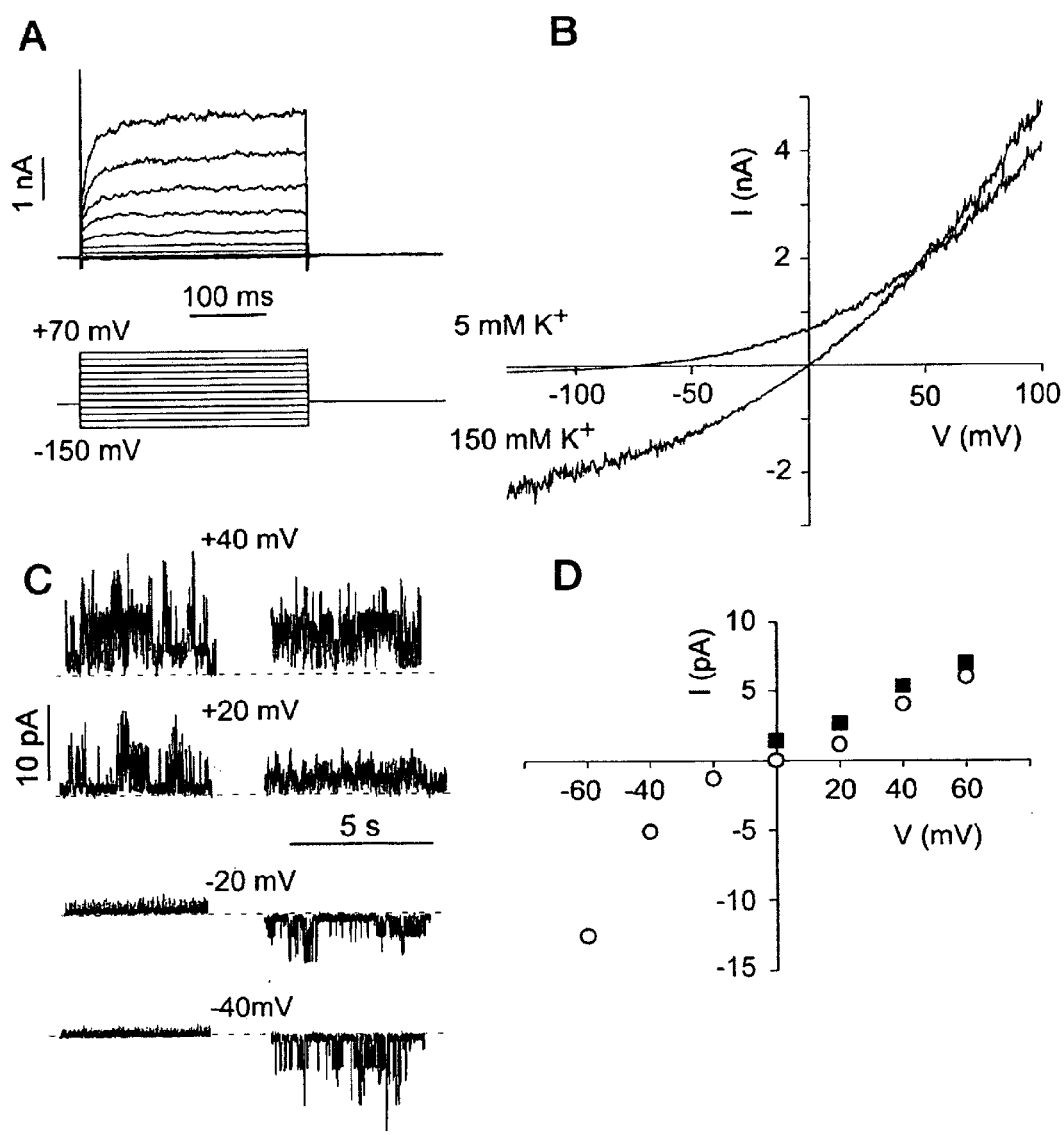
FIG. 3 shows graphic analyses of the biophysical properties of TREK2 currents.

TREK2-transfected COS cells display noninactivating currents (as shown in FIG. 3A) that are not present in control cells (not shown). The activation kinetics of TREK2 current are rapid. Depolarization pulses induce a two-step current composed of instantaneous and delayed components (as shown in FIG. 3A). The current-voltage (I-V) relationship is outwardly rectifying, and almost no inward currents were recorded in an external medium containing 5 mM $K^+$ (as shown in FIG. 3B). When cells are bathed in a $K^+$-rich solution (150 mM), an inward current is revealed and the reversal potential becomes 0 mV as expected for a $K^+$-selective channel. However, the I-V relationship is not linear and does not strictly fits the GHK equation for an open $K^+$-selective pore. The current has a tendency to saturate at very negative potentials. Two-step activation kinetics and outward rectification in symmetrical $K^+$ conditions have also been found for the TREK1 current (2, 17). Moreover like TREK1, TREK2 outward currents are more important in 150 mM $K^+$ than in 5 mM $K^+$ for depolarizations higher than +50 mV. This effect is unusual since an increase of external $K^+$ lowers the chemical driving force for outward $K^+$ flux and would be expected to decrease rather than increase the currents. For TREK1, this effect has been attributed to a stimulating effect of external $K^+$ as found for other types of $K^+$ channels (27, 28). In addition, TREK1 has been shown to be sensitive to external $Na^+$ ($Na^+_e$). When $Na^+_e$ was substituted by NMDG, TREK1 activity was strongly decreased (2). TREK2 is only partially inhibited by removing $Na^+_e$ (23% of inhibition, n=5, not shown). Single-channel properties of TREK2 are illustrated in FIGS. 3C and 3D. Basal channel activity in outside-out patches is characterized by a flickery bursting behaviour (as shown in FIG. 3C). In physiological $K^+$ conditions, the I-V relationship is outwardly rectifying and almost no inward currents were recorded as in whole-cell recording. In symmetrical conditions, inward currents were recorded in addition to outward currents with single-channel conductances of 128 pS at −40 mV and 100 pS at +40 mV (n=5) (as shown in FIGS. 3C and 3D). The single-channel I-V relationship is inwardly rectifying because the single-channel conductance increases for negative potentials. However, the channel open probability at negative potentials is lower than at positive potentials (Po=0.26 at −40 mV and Po=0.45 at +40 mV, n=5) and this explains why the currents are outwardly rectifying in the whole-cell configuration.

Stretch- and pH-Sensitivity of TREK2 Currents

Figure 4:
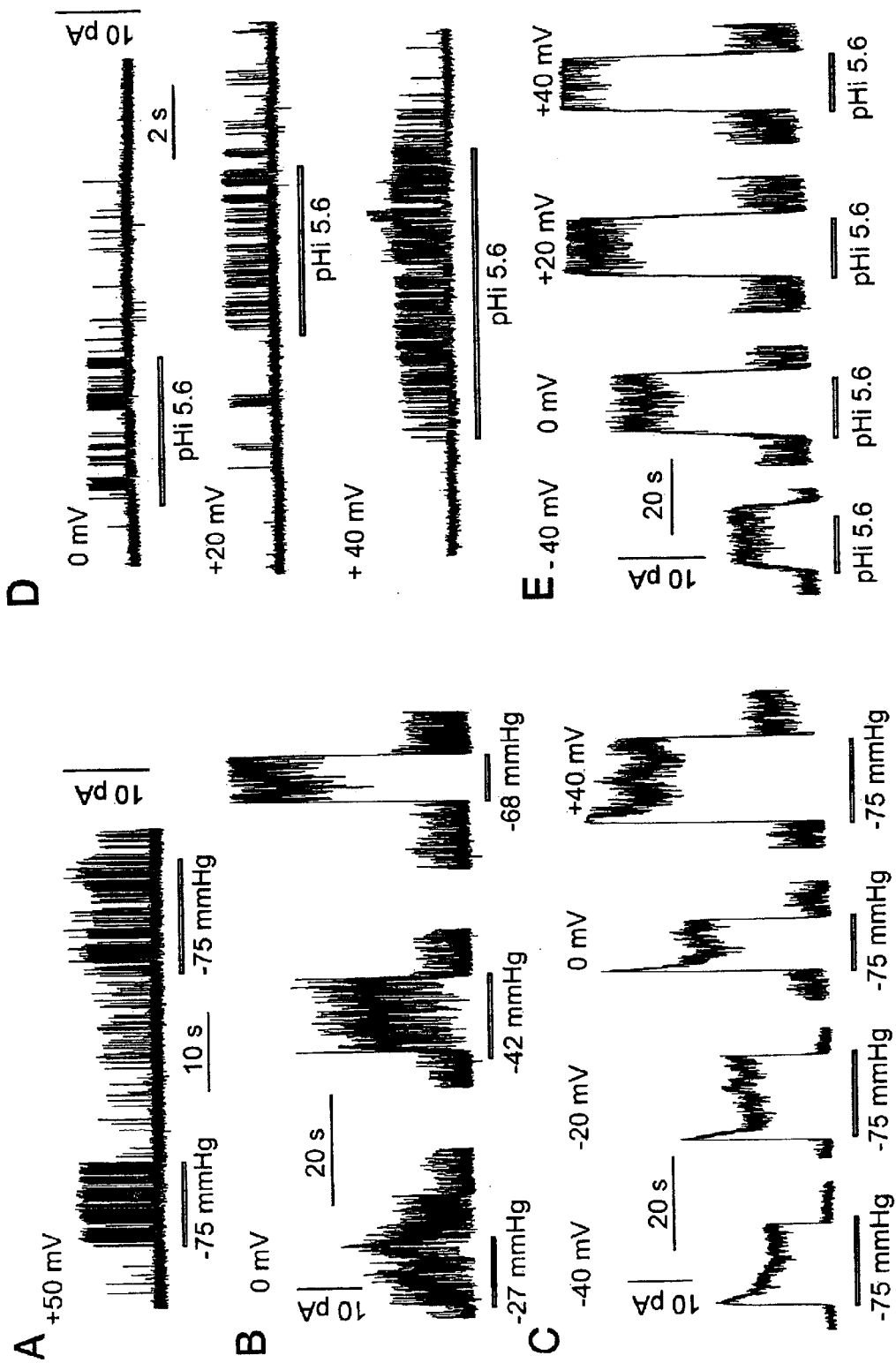
FIG. 4 shows the activation of TREK2 by a stretch of the membrane and by internal acidosis.

In addition to being modulated by polyunsaturated fatty acids, TREK2, like TREK1, is stimulated by a stretch of the membrane as well as by acidification of the intracellular medium. FIG. 4A shows that application of a negative pressure in the inside-out configuration induces a strong activation of TREK2 activity that is reversible. The activation is graded in function of the applied pressure (as shown in FIG. 4B). As shown for TREK1 and TRAAK (17, 18), stretch-induced TREK2 channel activity can be elicited at both negative and positive potentials and the level of activation increases with depolarization (as shown in FIG. 4C). FIG. 4D shows that intracellular acidification induces a strong increase of TREK2 channel activity. This effect is reversible and is observed at substantially all membrane potentials (as shown in FIG. 4E). A similar effect has been previously described for TREK1 (19). Acidification of the extracellular medium has no effect on the whole cell TREK2 current (less than 20% of inhibition at pH 6.5) (not shown).

Pharmacological Properties of TREK2 Currents

Figure 5:
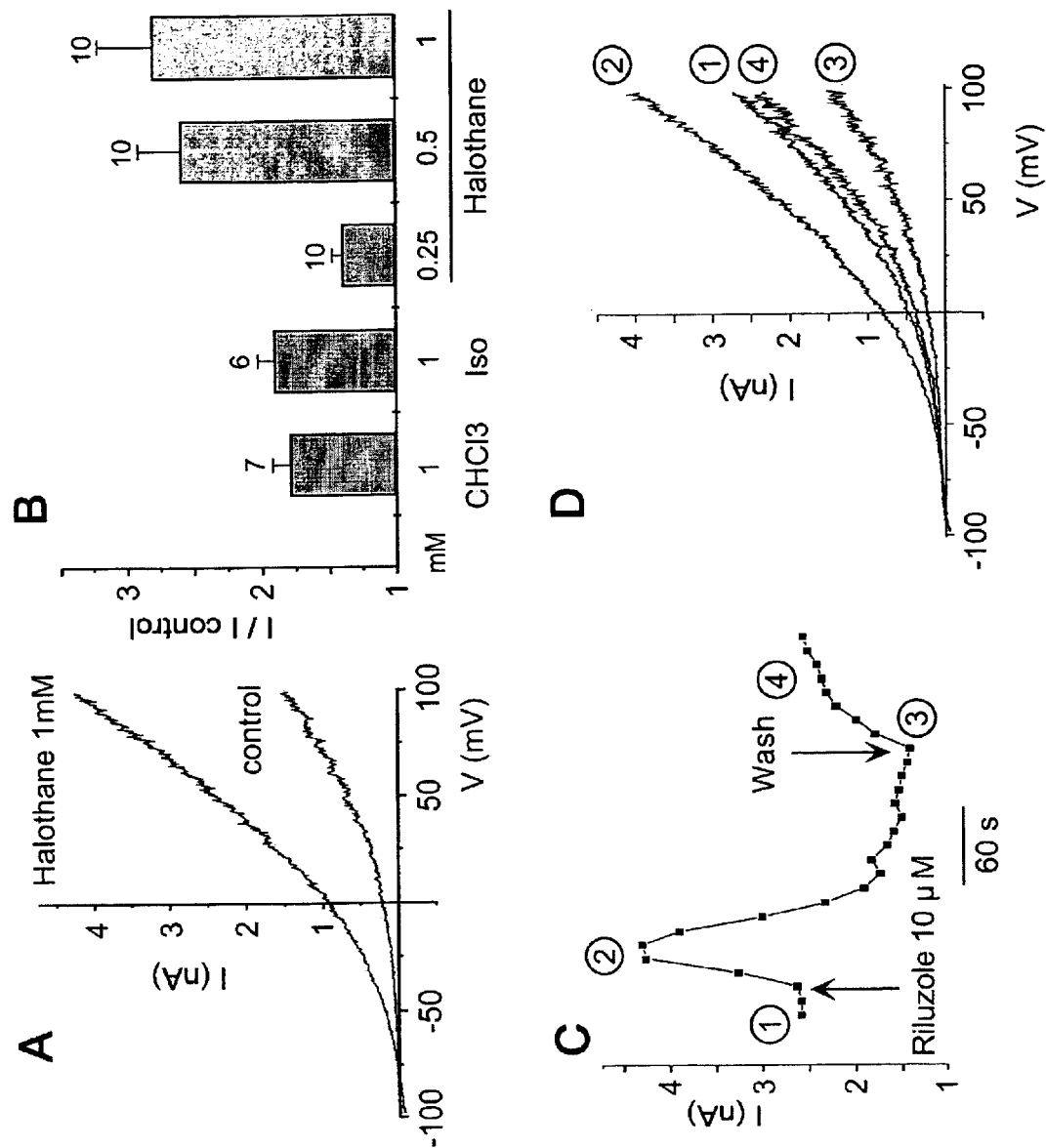
FIG. 5 shows the activation of TREK2 by volatile anesthetics and riluzole.

TREK2 currents are insensitive to tetraethylammonium (TEA, 10 mM) and $Ba^{2+}$ (1 mM). Quinidine inhibited the currents (50% of inhibition at 100 $\mu$M) (not shown). Like TREK1, TREK2 is stimulated by application of the inhalational anesthetics chloroform, halothane and isoflurane (as shown in FIGS. 5A and 5B). At a clinical dose of halothane (29), TREK2 is markely activated (1.4±0.1 fold increase at 0.25 mM, n=10 at +100 mV). The maximal halothane effect is nearly obtained at 0.5 mM (2.6±0.3, fold increase, n=10 at +100 mV). The efficiency of anesthetics is different between TREK1 and TREK2. For TREK2, halothane (2.3±0.3 fold increase at 1 mM, n=6 at 0 mV) is more efficient than isoflurane (1.9±0.1 fold increase at 1 mM, n=6) and chloroform (1.8±0.1 fold increase at 1 mM, n=7). For TREK1, chloroform is more effective than halothane and isoflurane at the same concentrations (1 mM) (16). FIGS. 5C and 5D show that TREK2 is also activated by application of the neuroprotective drug riluzole. As for TREK1, this activation is transient and is followed by a decrease of the activity corresponding to an inhibition. In the case of TREK1, this is due to an increase of the intracellular cAMP and a phosphorylation of the channel by PKA (30).

Activation of TREK2 by Fatty Acids and Inhibition by Intracellular cAMP

Figure 6:
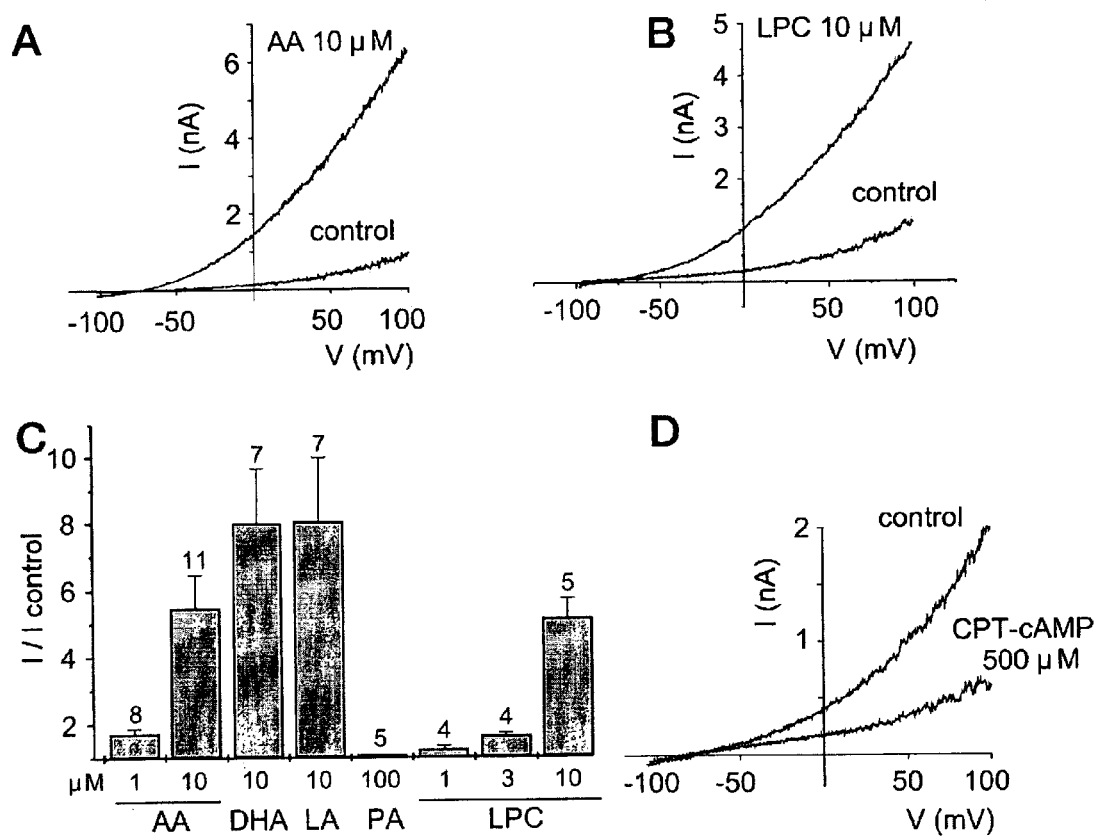
FIG. 6 shows the activation of TREK2 by polyunsaturated fatty acids and lysophosphatidylcholine and inhibition by cAMP.

FIG. 6A illustrates the strong stimulating effect of 10 $\mu$M arachidonic acid on TREK2 current (8.4±1.9 fold increase at 0 mV, n=6). This effect is reversible (not shown).

Like TREK1, TREK2 is activated by other polyunsaturated fatty acids, docosahexaenoic and linoleic acids, and by lysophosphatidylcholine, but not by the saturated fatty acid palmitic acid (as shown in FIGS. 6B and 6C) (17, 31). TREK2 is also activated by 10 $\mu$M lysophosphatidylinositol (5.1±0.6 fold increase at 0 mV, n=8). Application of the permeant CPT-cAMP (500 $\mu$M) led to 50% inhibition of TREK2 activity at 0 mV (50±5, n=8) (as shown in FIG. 6D). A similar inhibition is obtained by application of a mixture of 3-isobutyl-1- methylxanthine (IBMX, 1 mM)/forskolin (10 $\mu$M) to increase the intracellular cAMP level (72 ±10% of inhibition, n=8). This suggests that TREK2 as TREK1 is inhibited by PKA phosphorylation (16).

Figure 7:
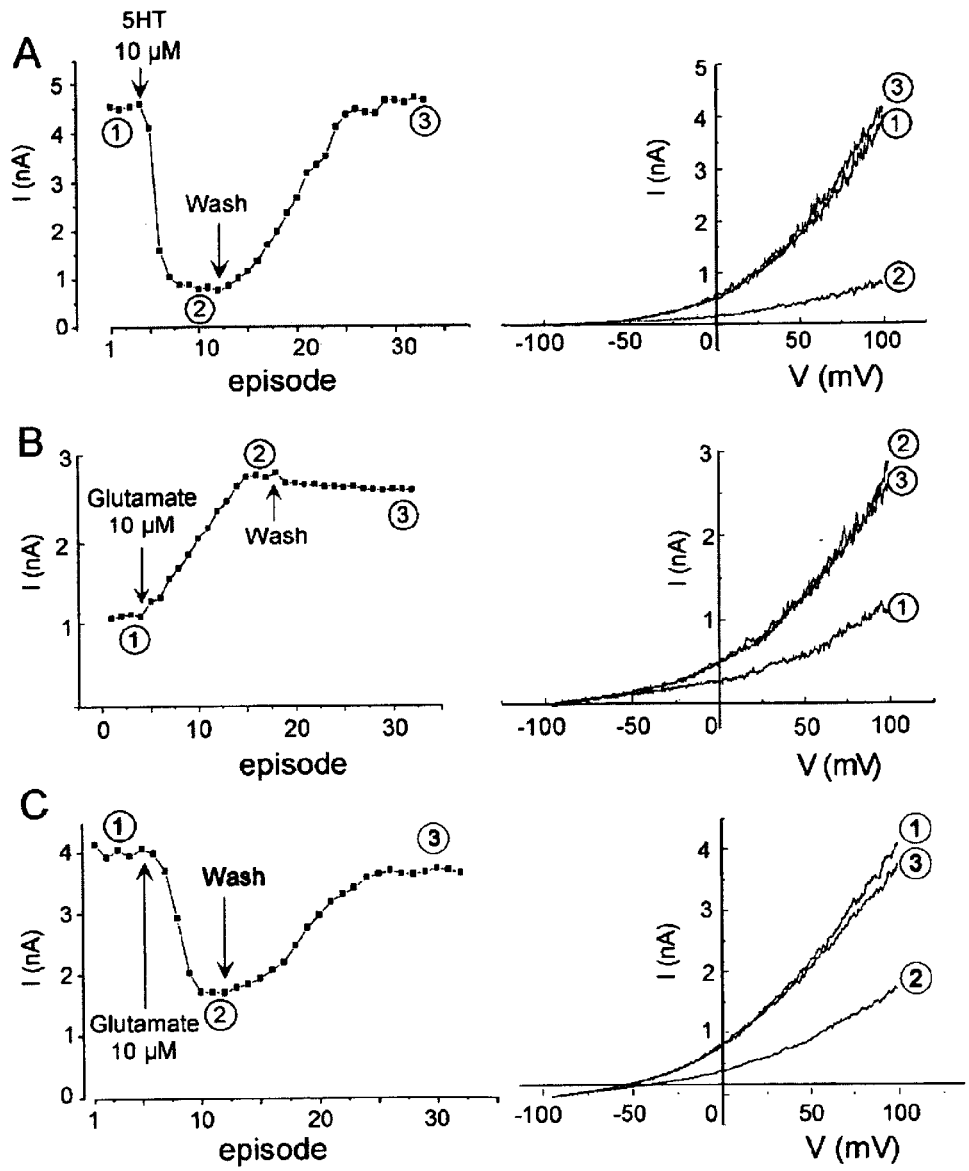
FIG. 7 shows the regulation of TREK2 by G-protein-coupled receptors.

Regulation of TREK2 by Co-Expression with Gs-, Gi- and Gq-Coupled Neurotransmitter Receptors TREK2 was co-expressed with 5HT4sR, a Gs-coupled receptor. The stimulation of the receptor by application of 5-HT is associated with a decrease of TREK2 activity, as expected for a receptor positively coupled to adenylate cyclase (as shown in FIG. 7A). Conversely, activation of the co-expressed Gi-coupled mGluR2 receptor by glutamate leads to a stimulation of TREK2 activity (as shown in FIG. 7B). The decrease of TREK2 activity by the stimulation of 5HT4sR is rapidly reversed after washing (as shown in FIG. 7A) while the TREK2 increase associated with mGluR2 is much slower to reverse (more than 10 minutes) (as shown in FIG. 7B). A third type of G-protein coupled receptor was co-expressed with TREK2. This receptor is the Gq-coupled mGluR1 receptor. Activation of mGluR1 by application of glutamate led to an inhibition of TREK2 activity that is rapidly reversed by washing (as shown in FIG. 7C). The Gq-protein is commonly associated with activation of phospholipase C and the consequent production of diacylglycerol (DAG) and inositol 1,4,5-triphosphate (IP 3). Ultimately, DAG leads to activation of PKC and IP 3 to an increase of intracellular $Ca^{2+}$. However, neither the application of the PKC-activator PMA (100 nM) nor the addition of $Ca^{2+}$ in the recording pipette (1 μM) were able to induce an inhibition of TREK2 (not shown).

All publications cited herein are hereby incorporated by reference as though each is recited here in its entirety.

REFERENCES

1. Lesage, F., Guillemare, E., Fink, M., Duprat, F., Lazdunski, M., Romey, G., and Barhanin, J. (1996) *EMBO J.* 15, 1004–1011
2. Fink, M., Duprat, F., Lesage, F., Reyes, R., Romey, G., Heurteaux, C., and Lazdunski, M. (1996) *EMBO J.* 15, 6854–6862
3. Duprat, F., Lesage, F., Fink, M., Reyes, R., Heurteaux, C., and Lazdunski, M. (1997) *EMBO J.* 16, 5464–5471
4. Leonoudakis, D., Gray, A. T., Winegar, B. D., Kindler, C. H., Harada, M., Taylor, D. M., Chavez, R. A., Forsayeth, J. R., and Yost, C. S. (1998) *J. Neurosci.* 18, 868–877
5. Kim, D., Fujita, A., Horio, Y., and Kurachi, Y. (1998) *Circ. Res.* 82, 513–518
6. Fink, M., Lesage, F., Duprat, F., Heurteaux, C., Reyes, R., Fosset, M., and Lazdunski, M. (1998) *EMBO J.* 17, 3297–3308
7. Reyes, R., Duprat, F., Lesage, F., Fink, M., Salinas, M., Farman, N., and Lazdunski, M. (1998) *J. Biol. Chem.* 273, 30863–30869
8. Salinas, M., Reyes, R., Lesage, F., Fosset, M., Heurteaux, C., Romey, G., and Lazdunski, M. (1999) *J. Biol. Chem.* 274, 11751–11760
9. Kim, Y., Bang, H., and Kim, D. (2000) *J. Biol. Chem.* 275, 9340–9347
10. Rajan, S., Wischmeyer, E., Liu, G. X., Preisig-Müller, R., Daut, J., Karschin, A., and Derst, C. (2000) *J. Biol. Chem* 275,16650–16657.
11. Lesage, F. and Lazdunski, M. (1999) in *Potassium Ion Channels: Molecular Structure, Function and Diseases.* (Kurachi, Y., Jan, L. Y., and Lazdunski, M. ed.) Vol. 46, pp. 199–222, Academic press, San Diego, Calif.
12. Premkumar, L. S., Gage, P; W., and Chung, S. H. (1990) *Proc. R. Soc. Lond. B.* 242, 17–22
13. Ordway, R. W., Singer, J. J., and Walsh Jr, J. V. (1991) *TINS* 14, 96–100
14. Kim, D., and Clapham, D. E. (1989) *Science* 244, 1174–1176
15. Kim, D. H., Sladek, C. D., Aguadovelasco, C., and Mathiasen, J. R. (1995) *J. Physiol.* (London) 484, 643–660
16. Patel, A. J., Honore, E., Lesage, F., Fink, M., Romey, G., and Lazdunski, M. (1999) *Nat. Neurosci.* 2, 422–426
17. Patel, A. J., Honoré, E., Maingret, F., Lesage, F., Fink, M., Duprat, F., and Lazdunski, M. (1998) *EMBO J.* 17, 4283–4290
18. Maingret, F., Fosset, M., Lesage, F., Lazdunski, M., and Honore, E. (1999) *J. Biol. Chem.* 274, 1381–1387
19. Maingret, F., Patel, A. J., Lesage, F., Lazdunski, M., and Honore, E. (1999) *J. Biol. Chem.* 274, 26691–26696
20. Reyes, R., Lauritzen, I., Lesage, F., Etaiche, M., Fosset, M., and Lazdunski, M. (2000) *Neuroscience* 95, 893–901
21. Altschul, S. F., Gish, W., Miller, W., Myers, E. W., and Lipman, D. J. (1990) *J. Mol. Biol.* 215, 403–410
22. Waldmann, R., Bassilana, F., de Weille, J., Champigny, G., Heurteaux, C., and Lazdunski, M. (1997) *J. Biol. Chem.* 272, 20975–20978
23. Arrighi, I., Lesage, F., Scimeca, J. C., Carle, G. F., and Barhanin, J. (1998) *FEBS Lett.* 425, 310–316
24. Lesage, F., Maingret, F., and Lazdunski, M. (2000) *FEBS Lett.* 137–140
25. Wang, Z. W., Kunkel, M. T., Wei, A., Butler, A., and Salkoff, L. (1999) *Ann. N. Y. Acad. Sci.* 868, 286–303
26. Lesage, F., and Lazdunski, M. (1998) *Genomics* 51, 478–479
27. Carmeliet, E. (1989) *Pflügers Arch.* 414, S88–92
28. Pardo, L. A., Heinemann, S. H., Terlau, H., Ludewig, U., Lorra, C., Pongs, O., and Stühmer, W. (1992) *Proc. Natl. Acad. Sci. USA* 89, 2466–2470
29. Lopes, C. M., Franks, N. P., and Lieb, W. R. (1994) *Nature* 367, 607–614
30. Duprat, F., Lesage, F., Patel, A. J., Fink, M., Romey, G., and Lazdunski, M. (2000) *Mol. Pharmacol.* 57, 906–912
31. Maingret, F., Patel, A. J., Lesage, F., Lazdunski, M., and Honoré, E. (2000) *J. Biol. Chem.* 275, 10128–10133
32. Bang, H., Kim, Y., and Kim, D. (2000) *J. Biol. Chem.* 275,17412–17419.
33. Millar, J. A., Baratt, A. P., Southan, A. P., Page, K. M., Fyffe, R. E. W., Robertson, B., and Mathie, A. (2000) *Proc. Natl. Acad. Sci. USA* 97, 3614–3618
34. Talley, E. M., Lei, Q., Sirois, J. E., and Bayliss, D. A. (2000) *Neuron* 25, 399–410

---

What is claimed is:

1. An isolated and purified protein comprising a mammalian $K^+$ channel with two pore domains, wherein said channel produces currents whose current-voltage relationship is weakly inwardly rectifying in high symmetrical $K^+$ conditions, and wherein said channel comprises the amino acid sequence of SEQ ID NO: 2.

2. The protein of claim 1, wherein said channel is a human $K^+$ channel.

3. The protein of claim 1 consisting essentially of the amino acid sequence of SEQ ID NO: 2.

4. The mammalian $K^+$ channel of claim 1, wherein said high symmetrical $K^+$ conditions is a $K^+$-rich external medium of about 150 mM.

* * * * *